United States Patent [19]

Lang et al.

[11] Patent Number: 5,690,921
[45] Date of Patent: Nov. 25, 1997

[54] HAIR FIXING COMPOSITION IN THE FORM OF AN AQUEOUS SOLUTION, FOAM OR GEL

[75] Inventors: Günther Lang, Reinheim; Thomas Clausen, Alsbach, both of Germany

[73] Assignee: Wella Aktiengesellschaft, Darmstadt, Germany

[21] Appl. No.: 561,957

[22] Filed: Nov. 22, 1995

Related U.S. Application Data

[63] Continuation of Ser. No. 244,365, May 24, 1994, abandoned.

[30] Foreign Application Priority Data

Oct. 15, 1992 [DE] Germany ............ 42 34 743.2

[51] Int. Cl.$^6$ .................................................. A61K 7/11
[52] U.S. Cl. ............ 424/70.13; 424/47; 424/70.21; 424/70.12; 424/70.31; 424/78.03; 424/DIG. 1; 424/DIG. 2
[58] Field of Search ............ 424/401, 47, 70.13, 424/70.21, 70.31, 70.12, 78.03, DIG. 1, DIG. 2

[56] References Cited

U.S. PATENT DOCUMENTS

| | | | |
|---|---|---|---|
| 2,305,356 | 12/1942 | Luckenbach | 132/202 |
| 2,857,314 | 10/1958 | Philips, Jr. | 424/47 |
| 3,928,558 | 12/1975 | Cheesman et al. | 424/47 |
| 3,954,960 | 5/1976 | Valan | 424/47 |
| 4,223,009 | 9/1980 | Chakrabarti | 424/47 |
| 4,871,529 | 10/1989 | Sramek | 424/47 |
| 4,938,950 | 7/1990 | Lang et al. | 424/47 |

*Primary Examiner*—George F. Lesmes
*Assistant Examiner*—Robert H. Harrison
*Attorney, Agent, or Firm*—Michael J. Striker

[57] ABSTRACT

The hair fixing composition is in the form of an aqueous solution, foam or gel and contains from 0.1 to 5 percent by weight of one or more film-forming natural polymers, from 5 to 60 percent by weight of one or more water-soluble, halogen-free organic solvents, from 30 to 95% by weight water and from 0.05 to 2 percent by weight of one or more of the following compounds which are insoluble in water at room temperature but soluble in the composition: a $C_8$- to $C_{20}$-alkanediol, a $C_8$- to $C_{20}$-alkanetriol, a monoglyceride of saturated or unsaturated $C_{12}$- to $C_{20}$-fatty acids, a monodiglyceride of saturated or unsaturated $C_{12}$- to $C_{20}$-fatty acids, a $C_{12}$- to $C_{20}$-fatty alcohol ethoxylated with from 2 to 3 moles of ethylene oxide, a polysiloxane/polyether copolymer having a cloud point at a temperature of less than 20° C., a polyoxyethylene/polyoxypropylene block polymer and a polyoxyethylene/polyoxybutylene block polymer. The organic solvent and the water insoluble compound component are present in a weight ratio of from 1000:1 to 2.5:1.

7 Claims, No Drawings

HAIR FIXING COMPOSITION IN THE FORM OF AN AQUEOUS SOLUTION, FOAM OR GEL

This is a continuation of application Ser. No. 08/244,365 filed May 24, 1994, abandoned.

BACKGROUND OF THE INVENTION

The present invention is directed to a composition for fixing hair based on an aqueous solution of at least one film-forming natural or synthetic polymer containing a combination of a water-soluble, halogen-free organic solvent and at least one determined compound which is insoluble in water at room temperature, but is soluble in the composition for fixing hair.

Compositions for fixing hair must satisfy a great many requirements. For example, this composition must provide hair with a firm yet flexible hold without impairing the natural feel of the hair. The fixing characteristics of the composition must also withstand high atmospheric humidity without making hair feel sticky. But, at the same time, it must also be ensured that hair which is damaged by repeated bleaching, permanent waving, dyeing or frequent washing with degreasing hair cleaning agents can be combed easily after applying the hair fixing composition, particularly when the hair is wet. Hair which has been treated with the fixing composition should, when dry, have an attractive shine in addition to a good hold of the hairstyle.

Until now, it has not been possible for conditioning ingredients which facilitate combing to be added to hair fixing compositions in the form of aqueous or aqueous-alcoholic solutions in sufficient quantities without negatively affecting the fixing characteristics and homogeneity of the compositions.

For this reason, two-phase hair fixing compositions, so-called shaking emulsions, have also been provided in the past. In these shaking emulsions, the aqueous or aqueous-alcoholic fixing phase was covered by a second, oily phase, e.g. paraffin oil, which contained conditioning ingredients and was insoluble in water. An unstable emulsion was produced by shaking prior to application of this composition. However, such shaking emulsions have the disadvantage that the instability of the formed emulsion leads to uneven distribution of the fixing and conditioning components on the hair. Therefore, hair fixing compositions in the form of a shaking emulsions were unsatisfactory for fixing hair and simultaneously facilitating the combing of wet hair. In addition, such shaking emulsions are only available in single-application packages, which is inadvisable in ecological respects and for prevention of waste.

SUMMARY OF THE INVENTION

Therefore, it is an object of the present invention to provide a composition for fixing hair based on an aqueous solution which does not have the disadvantages of the known compositions, that is, one which provides the hair with a good hold while facilitating combing, particularly with wet hair.

Surprisingly, it has now been found that a composition for fixing hair which satisfies all of the requirements for a composition of this kind in an outstanding manner is obtained by adding a combination of at least one water-soluble, halogen-free organic solvent and a compound which is insoluble in water at room temperature, but soluble in the composition for fixing hair, to an aqueous solution containing at least one film-forming polymer.

The subject matter of the present invention is therefore a composition for fixing hair based on an aqueous solution of at least one film-forming natural or synthetic polymer containing a combination of (A) at least one water-soluble, halogen-free organic solvent and (B) 0.05 to 2 percent by weight of at least one compound which is insoluble in water at room temperature, but soluble in the composition, which is selected from $C_8$- to $C_{20}$-alkanediols, $C_8$- to $C_{20}$-alkanetriols, monoglycerides or monodiglycerides of saturated or unsaturated $C_{12}$- to $C_{20}$-fatty acids, $C_{12}$- to $C_{20}$-fatty alcohols ethoxylated with 2 or 3 moles of ethylene oxide, polysiloxane/polyether copolymers with a cloud point at a temperature of less than 20° Celsius, polyoxyethylene/polyoxypropylene block polymers or polyoxyethylene/polyoxybutylene block polymers, where the weight ratio of component (A) to component (B) is 1000:1 to 2.5:1, preferably 100:1 to 2.5:1.

In the present disclosure, room temperature is understood as a temperature of 20° to 25° Celsius.

The composition for fixing hair according to the present invention has good fixing properties and simultaneously causes a surprising and marked improvement in combability, particularly of wet hair, and in the shine and feel of the hair when dry.

In particular, the gliding action of the comb or brush in wet hair after applying the composition according to the invention is substantially improved so that blow drying or winding on water wave curlers is substantially facilitated.

The water-soluble, halogen-free organic solvent of component (A) is preferably selected from $C_1$- to $C_4$-alcohols such as ethanol, propanol, isopropanol, $C_1$- to $C_4$-glycols such as ethylene glycol or propylene glycol, polyethylene glycol esters with $C_2$- to $C_{20}$-carboxylic acids, liquid polyethylene glycols, polyethylene glycol alkyl ethers or $C_1$- to $C_4$-alcohols, simple or mixed ketones of $C_1$- to $C_5$-alcohols such as acetone or methyl ethyl ketone, particularly preferably aliphatic $C_1$- to $C_4$-alcohols, $C_1$- to $C_4$-glycols, polyethyl glycol esters with $C_2$- to $C_{20}$-carboxylic acids, liquid polyethylene glycols or mixtures thereof.

The composition according to the invention preferably contains 5 to 60 percent by weight, preferably 10 to 50 percent by weight, of the water-soluble, halogen-free organic solvent of component (A).

The water-insoluble $C_8$- to $C_{20}$-alkanediol or water-insoluble $C_8$- to $C_{20}$-alkanetriol of component (B) contained in the composition according to the invention is preferably water-insoluble straight-chain or branched saturated or unsaturated 1,2-$C_8$- to $C_{20}$-alkanediols or 1,2,3-$C_8$- to $C_{20}$-alkanetriols such as 1,2-octanediol, 1,2-dodecanediol, 1,2-hexadecanediol or 1,2,3-trihydroxy-3,7,11,15-tetramethylhexadecane. Of the water-insoluble alkanediols and alkanetriols suitable as component (B), 1,2,3-trihydroxy-3,7,11,15-tetramethylhexadecane which is sold by Hoffmann-La Roche, Basel, Switzerland, under the trade name Phytantriol® is particularly preferred.

The monoglycerides or monodiglycerides of saturated $C_{12}$- to $C_{20}$-fatty acids of component (B) of the composition according to the invention are preferably glyceryl monolaurate, glyceryl monooleate or palm kernel oil monoglyceride.

Commercial products with a monoglyceride proportion of 80% are preferably used as glyceryl monolaurate or glyceryl monooleate, while commercial products with a monoglyceride proportion of 60% are preferable as palm kernel oil monoglyceride as component (B).

The $C_{12}$- to $C_{20}$-fatty alcohol of component (B) of the composition according to the invention which is ethoxylated with 2 or 3 moles ethylene oxide is preferably lauryl alcohol, myristyl alcohol, cetyl alcohol or stearyl alcohol or mixtures thereof which are ethoxylated with 2 or 3 moles ethylene oxide, but preferably lauryl alcohol ethoxylated with 2 or 3 moles ethylene oxide.

The polysiloxane/polyether copolymer reaching cloud point at a temperature of less than 20° Celsius (measured in 4-percent aqueous solution) contained in component (B) of the composition according to the invention is preferably dimethylpolysiloxane/polyethylene oxide/polypropylene oxide copolymer with a cloud point of 10° Celsius which is sold, for example, by Th. Goldschmidt AG, Essen, Germany, as Abil B 8852®.

Preferred polyoxyethylene, polyoxypropylene block polymers which may be contained in the composition according to the invention as component (B) are those having a polyoxyethylene proportion of 10% of the total molecular weight sold, for example, by BASF, Ludwigshafen, Germany, under the trade names Pluronic L 61®, Pluronic L 81®, Pluronic L 101® and Pluronic L 121®.

In a preferred embodiment of the composition according to the invention, the compound of component (B) which is insoluble in water at room temperature but soluble in the composition is selected from 1,2-octanediol, 1,2-dodecanediol, 1,2-hexadecanediol, 1,2,3-trihydroxy-3,7,11,15-tetramethylhexadecane, glyceryl monolaurate, glyceryl monooleate, palm kernel oil monoglyceride, lauryl alcohol ethoxylated with 2 or 3 moles ethylene oxide, dimethylpolysiloxane/polyethylene oxide/polypropylene oxide copolymers with a cloud point at 10° Celsius, and polyoxyethylene, polyoxypropylene block polymers with a polyethylene oxide proportion of 10% of the total molecular weight.

The composition according to the invention preferably contains 0.1 to 0.5 percent by weight of component (B).

The composition according to the invention contains film-forming natural or synthetic polymers conventionally used for hair fixing compositions, e.g. anionic polymers such as homopolymers or copolymers of acrylic acid or methacrylic acid, copolymerizates of acrylic acid and acrylamides and copolymers based on alkyl vinyl ethers and maleic acid monoalkylesters; amphoteric polymers such as copolymerizates of octylacrylamide, acrylate and butylaminonmethylmethacrylate; cationic polymers such as vinylimidazolinium/vinylpyrrolidone copolymers; nonionic polymers such as vinylpyrrolidone homopolymers, vinylpyrrolidone/vinyl acetate copolymers or terpolymers of vinylpyrrolidone, vinyl acetate and vinylpropionate; or natural film-forming polymers such as chitin derivatives, chitosan, chitosan derivatives and chitosan salts, e.g. hydroxypropyl chitosan, hydroxybutyl chitosan, shellac, alginate, gelatine, pectin, cellulose derivatives such as hydroxyethylcellulose or hydroxypropylcellulose or mixtures thereof.

The composition according to the invention preferably contains at least one natural polymer selected from chitin derivatives, chitosan, chitosan derivatives and chitosan salts alone or in combination with at least one synthetic film-forming polymer.

The film-forming polymers contained in the composition according to the invention, insofar as these polymers contain acid groups, are used in 50-percent to 100-percent neutralized form using organic amines or alkanolamines, preferably with 2-amino-2-methyl-1-propanol, 2-amino-1-butanol or triisopropylamine.

The composition according to the invention preferably contains the film-forming natural or synthetic polymer in a quantity of 0.1 to 5 percent by weight, particularly 0.5 to 2.5 percent by weight.

If desired, the composition according to the invention for fixing hair can dye or tint the hair at the same time when it contains dyestuffs which are directly absorbed in the hair. Such preparations are known commercially, for example, as dye fixing compositions or tinting fixing compositions. They contain, in addition, conventional dyes which are absorbed directly in the hair, e.g. aromatic nitro dyes such as 1,4-diamino-2-nitrobenzene, picramic acid, 1-hydroxy-2-amino-4-nitrobenzene and 1,4-bis(2-hydroxyethyl)amino-2-nitro-5-chlorobenzene, azo dyes such as Acid Brown 4 (C.I. 14,805), anthraquinone dyes such as Disperse Violet 4 (C.I. 61,105) and triphenylmethane dyes such as Basic Violet I (C.I. 42,535), Basic Violet 14 (C.I. 42,510) or Basic Blue 7 (C.I. 42,595: 1). Depending on their substituents, these dyes can have an acidic, nonionic or basic character. The total concentration of such dyes in the composition according to the invention is generally approximately 0.01 to 2.0 percent by weight.

The composition according to the invention is in the form of an aqueous preparation, in particular a solution, foam or gel; the water content of the composition is preferably 30 to 95 percent by weight.

The composition according to the invention for fixing hair can take the form of a nonaerosol foam which can be sprayed by a suitable mechanically operated spraying device.

By mechanically operated spraying device is meant devices which spray liquids without using liquefied propellants. For example, a suitable mechanical spray device can be a spray pump or a flexible container which is provided with a spray valve and contains the aforementioned cosmetic composition under pressure. This flexible container expands and the composition can be dispensed in a continuous manner from this container due to the contraction of the flexible container by opening the spray valve.

The composition according to the invention can also be introduced into a container under pressure with the use of a propellant, the preparation being dispensed easily as a foam by means of a valve provided with a dispensing nozzle and conveniently distributed in the hair. Some examples of suitable propellants are highly volatile hydrofluorochlorocarbons such as difluorochloromethane or trichloromonofluoromethane, tetrafluorodichloroethane or low alkanes such as n-butane, i-butane and propane, or dimethyl ether and other gaseous propellants, e.g. $N_2$, $N_2O$ and $CO_2$, at the appropriate pressures, as well as mixtures of the aforementioned compounds. The propellants are advisably contained in this composition in quantities of approximately 2 to 10 percent by weight.

Further, the composition for fixing hair, according to the invention, can contain common cosmetic additives such as anionic, cationic, amphoteric or nonionic wetting agents and emulsifiers, e.g. $C_{12}$- to $C_{18}$-alkyl ether sulfates, alkyltrimethylammonium salts, alkylpyridinium salts, carboxyl derivatives of imidazole, N-alkylsulfobetaine or polyglyceryl ether of saturated or unsaturated fatty alcohols and alkylphenols in quantities of approximately 0.01 to 3 percent by weight, as well as preservatives such as salicylic acid or mandelic acid in quantities of 0.01 to 0.7 percent by weight, ingredients for controlling dandruff such as zinc pyridinethion, hair-grooming ingredients such as esters of fatty acid, fatty alcohols, lanolin derivatives or pantothenic acid in quantities of approximately 0.01 to 3 percent by weight, waterproofing agents such as silicone oils, e.g. polydimethyisiloxane, polymethylphenylsiloxane or cyclomethicone, emollients such as phthalic acid ester or alkyl citrates, cationic polymers such as cationic cellulose derivatives in quantities of 0.01 to 0.2 percent by weight, as well as complexing agents, foam stabilizers, buffers, light stabilizers or perfume oils in quantities of approximately 0.01 to 0.8 percent by weight.

The composition according to the invention preferably contains 0.01 to 2 percent by weight of at least one conventional cosmetic ingredient for fixing hair.

Approximately 5 to 20 g of the composition according to the invention are distributed in the hair, normally after shampooing the hair and drying it with a towel. The hair is then combed and immediately blown dry or first coiled on water wave curlers and then dried.

The following examples explain the subject matter of the invention in more detail.

EXAMPLES

Example 1

Hair Fixing Composition

| | |
|---|---|
| 0.60 g | chitosan |
| 0.50 g | oleyl alcohol ethoxylated with 3 moles ethylene oxide |
| 1.52 g | formic acid |
| 0.75 g | perfume oil |
| 16.00 g | isopropanol |
| 80.63 g | water |
| 100.00 g | |

Example 2

Hair Fixing Composition

| | |
|---|---|
| 0.60 g | chitosan |
| 0.50 g | oleyl alcohol ethoxylated with 2 moles ethylene oxide |
| 1.52 g | formic acid |
| 0.75 g | perfume oil |
| 24.00 g | isopropanol |
| 72.63 g | water |
| 100.00 g | |

Example 3

Hair Fixing Composition

| | |
|---|---|
| 0.60 g | chitosan |
| 0.50 g | oleyl alcohol ethoxylated with 3 moles ethylene oxide |
| 1.52 g | formic acid |
| 0.75 g | perfume oil |
| 12.00 g | isopropanol |
| 84.63 g | water |
| 100.00 g | |

Example 4

Hair Fixing Composition

| | |
|---|---|
| 2.00 g | polyvinylpyrrolidone |
| 0.20 g | chitosan |
| 0.45 g | oleic acid monoglyceride |
| 0.90 g | perfume oil |
| 28.00 g | isopropanol |
| 68.45 g | water |
| 100.00 g | |

Example 5

Hair Fixing Composition

| | |
|---|---|
| 2.00 g | polyvinylpyrrolidone |
| 0.20 g | chitosan |
| 0.50 g | dimethylpolysiloxane/polyethylene oxide/polypropylene oxide copolymer (e.g., Abil B 8852 ® manufactured by Th. Goldschmidt, Germany) |
| 0.90 g | perfume oil |
| 33.00 g | isopropanol |
| 63.40 g | water |
| 100.00 g | |

Example 6

Wet Gel

| | |
|---|---|
| 0.40 g | dimethylpolysiloxane/polyethylene oxide/polypropylene oxide copolymer (e.g. Abil B 8852 ® manufactured by Th. Goldschmidt, Germany) |
| 0.40 g | acrylic acid polymer |
| 1.00 g | vinylpyrrolidone/vinyl acetate copolymer |
| 0.60 g | sorbitan monopalmitate ethoxylated with 40 moles ethylene oxide |
| 0.20 g | perfume oil |
| 0.33 g | ammonia, 25-percent aqueous solution |
| 29.41 g | ethanol |
| 67.66 g | water |
| 100.00 g | |

Example 7

Hair Fixing Foam

| | |
|---|---|
| 2.800 g | chitosan |
| 0.190 g | glyceryl monolaurate |
| 0.200 g | cetyl trimethylammonium chloride |
| 0.688 g | formic acid |
| 0.200 g | perfume oil |
| 22.000 g | ethanol |
| 73.922 g | water |
| 100.000 g | |

Example 8

Hair Fixing Foam

```
2.800 g  chitosan
0.200 g  1,2-lauryldiol
0.200 g  cetyl trimethylammonium chloride
0.688 g  formic acid
0.200 g  perfume oil
22.000 g ethanol
73.912 g water
─────────
100.000 g
```

Example 9

Hair Fixing Foam

```
2.800 g  chitosan
0.200 g  cetyl alcohol ethoxylated with 2 moles ethylene oxide
0.200 g  cetyl trimethylammonium chloride
0.688 g  formic acid
0.200 g  perfume oil
22.000 g ethanol
73.912 g water
─────────
100.000 g
```

Example 10

Hair Fixing Foam

```
2.800 g  chitosan
0.200 g  oleyl alcohol ethoxylated with 3 moles ethylene oxide
0.200 g  cetyl trimethylammonium chloride
0.688 g  formic acid
0.200 g  perfume oil
22.000 g ethanol
73.912 g water
─────────
100.000 g
```

100 g of the composition according to Example 7, 8, 9 or 10 are introduced under pressure into a container commonly used for cosmetic compositions with a foam nozzle with 10 g of propane/butane. The hair fixing foams according to Examples 7, 8, 9 and 10 are applied in the usual manner for such compositions.

Example 11

Tinting Foam

```
0.5000 g  glyceryl monolaurate
0.5000 g  cetyl trimethylammonium chloride
0.5000 g  distearyl dimethyl ammonium chloride
0.4000 g  hydroxyethylcellulose
0.0010 g  Solvent Blue 5, C.I. 42,595:1
0.0007 g  Basic Violet 14, C.I. 42,510
10.0000 g ethanol
0.2000 g  perfume oil
87.8983 g water
──────────
100.0000 g
```

100 g of the composition according to Example 11 are introduced with 10 g of propane/butane in a pressurized container with foam nozzle as conventionally used for cosmetic compositions. After shampooing and towel drying the hair, 20 g of the foam are distributed in the hair. The hair is then set and dried. The hair is tinted a brilliant silver shade and fixed.

COMPARISON EXAMPLES

Example A

On either side of a central part in the hair of a test subject, the composition according to the invention in Examples 1, 2 and 3 containing lauryl or oleyl alcohol ethoxylated with 2 or 3 moles ethylene oxide and the composition according to Example II which is not the subject of the invention and which contains oleyl alcohol ethoxylated with 10 moles ethylene oxide are compared with the composition according to Example I which is not the subject of the invention and which contains no ethoxylated fatty alcohol. The compositions according to Examples I and II which are not the subject of the invention have the following composition:

TABLE 1

| Example | I | II |
|---|---|---|
| chitosan | 0.60 g | 0.60 g |
| oleyl alcohol ethoxylated with 10 moles ethylene oxide | — | 0.50 g |
| formic acid | 1.52 g | 1.52 g |
| perfume oil | 0.75 g | 0.75 g |
| isopropanol | 16.00 g | 16.00 g |
| water | 81.13 g | 80.63 g |
| | 100.00 g | 100.00 g |

The shampooed, towel-dried hair of 8 test subjects with medium-long hair was treated with the composition according to Example I and a composition according to Examples 1, 2, 3 or II in a parallel test. To obtain clearly defined results and exclude the influence of hair quality differing from one test subject to the next, the hair was parted in the middle, one half being treated with 8 g of the composition according to Example I and the other side being treated with the same amount of one of the compositions according to Examples 1, 2, 3 or II. Each half of the hair was then combed and judged on the basis of combability when wet and development of foam during combing. The hair was then coiled on water wave curlers and dried. After removing the curlers, the hair was styled and the ease of styling and hold of the hairstyle was judged.

The results of the appraisal by hairstyling experts are compiled in the following Table 2. Evaluation was based on combability when wet, foam development and ease of styling and hold of the hairstyle according to the following grading system:

TABLE 2

| Example | II | 1 | 2 | 3 |
|---|---|---|---|---|
| combability when wet | 0 | + | ++ | ++ |
| foam development when combing | 0 | − | − | − |
| ease of styling and hold of hair style | 0 | 0 | 0 | 0 |

Grades:
++ great improvement over Example I
+ distinct improvement over Example I
0 no difference from Example I
− inferior to Example I The results of the preceding comparison tests with Examples 1, 2 and 3 according to the invention and with Example II which is not the subject of the invention show that the compositions according to the invention according to Examples 1, 2 and 3 achieved a surprising improvement in combability when wet while retaining ease of styling and a good hold of the hairstyle compared with the compositions according to Examples I and II. In addition, the foam development during combing which was judged negatively in conventional compositions for fixing hair such as the compositions according to Examples I and II was reduced in the compositions according to the invention.

Example B

The mechanical-physical assessment of the improvement in the combability of wet hair when applying the compositions according to Examples 4 and 5, according to the invention, was based on the measurement of combing force similar to the methods described in M. L. Garcia, J. Diaz, "Combability Measurements of Human Hair", *J. Soc. Cosmet. Chem.* 27 (1976), pages 379 to 398 in comparison to the corresponding Examples III and IV which are not the subject of the invention and have the following composition:

| Example | III | IV |
| --- | --- | --- |
| polyvinylpyrrolidone | 2.00 g | 2.00 g |
| chitosan | 0.20 g | 0.20 g |
| perfume oils | 0.90 g | 0.90 g |
| isopropanol | 28.00 g | 33.00 g |
| water | 68.90 g | 63.90 g |
| | 100.00 g | 100.00 g |

In each case, a strand of European human hair weighing approximately 2 g was moistened with water and clamped in a measuring device. 0.25 ml of each composition according to Examples 4, 5, III or IV was uniformly applied to the strand of hair. The average combing force required for combing the strand of hair was then measured.

The average combing force was measured with the Model 1122 tension testing device manufactured by Intron for 3 different strands of hair (weight 2 g, length 10 cm) at 21° Celsius using 3 Teflon-coated aluminum combs rotating on a belt (distance between comb teeth: 1 mm).

The average measurement values for the 3 strands of hair are compiled in Table 3.

TABLE 3

| Example | III | 4 | reduction in combability (%) |
| --- | --- | --- | --- |
| average combing force (Nmm) | 5.1 | 2.8 | 45 |

| Example | IV | 5 | reduction in combability (%) |
| --- | --- | --- | --- |
| average combing force (Nmm) | 5.2 | 3.4 | 35 |

As can be seen from Table 3, the average combing force is substantially lower when using the composition, according to the invention, of Examples 4 and 5 than in the corresponding Comparison Examples III and IV.

Example C

The mechanical-physical assessment of the improvement in combability of hair in the wet and dry states by applying the composition according to the invention in Examples 12, 13, 14 and 15 was effected in a manner analogous to the methods used in the literature cited in Example B in comparison to Examples V to X which are not the subject of the invention.

In each case, a strand of European human hair was moistened with water and clamped in the measuring device. The average combing force required for combing the strand of (wet) hair was then measured. The strands of hair were then dried and the maximum combing force required for combing the (dry) hair strands was measured again. The maximum combing force was measured with the Intron Model 1122 tension testing device for 3 different strands of hair at 21° Celsius using 3 Teflon-coated aluminum combs rotating on a belt (distance between comb teeth: 1 mm).

Tables 4, 5 and 6 show the ingredients of the compositions according to the invention in Examples 12, 13, 14 and 15 and the comparison examples V to X which are not the subject of the invention and the average values of the measured maximum combing force for wet and dry hair.

TABLE 4

| Example | 12 | 13 | V | VII |
| --- | --- | --- | --- | --- |
| chitosan | 1.00 g | 1.00 g | 1.00 g | 1.00 g |
| lauryl alcohol ethoxylated with 2 moles ethylene oxide | 0.50 g | — | — | — |
| lauryl alcohol ethoxylated with 3 moles ethylene oxide | — | 0.50 g | — | — |
| lauryl alcohol ethoxylated with 4 moles ethylene oxide | — | — | 0.50 g | — |
| ethanol | 35.00 g | 30.00 g | 20.00 g | 40.00 g |
| pyrrolidone carboxylic acid | 0.85 g | 0.85 g | 0.85 g | 0.85 g |
| water | 62.65 g | 67.65 g | 77.65 g | 58.15 g |
| | 100.00 g | 100.00 g | 100.00 g | 100.00 g |
| maximum combing force - wet - (mN) | 236 | 255 | 306 | 354 |
| maximum combing force-dry-(mN) | 410 | 419 | 687 | 1402 |

TABLE 5

| Example | 14 | VI | VII |
| --- | --- | --- | --- |
| chitosan | 1.00 g | 1.00 g | 1.00 g |
| cetyl alcohol ethoxylated with 2 moles ethylene oxide | 0.50 g | — | — |
| cetyl alcohol ethoxylated with 5 moles ethylene oxide | — | 0.50 g | — |
| ethanol | 53.00 g | 45.00 g | 40.00 g |
| pyrrolidone carboxylic acid | 0.85 g | 0.85 g | 0.85 g |
| water | 44.65 g | 52.65 g | 58.15 g |
| | 100.00 g | 100.00 g | 100.00 g |
| maximum combing force - wet - (mN) | 239 | 290 | 354 |
| maximum combing force - dry - (mN) | 679 | 787 | 1402 |

TABLE 6

| Example | 15 | VIII | IX | X |
| --- | --- | --- | --- | --- |
| dimethylpolysiloxane/ polyethylene oxide/ polypropylene oxide copolymer with a cloud point of 10° Celsius | 0.50 g | — | — | — |

TABLE 6-continued

| Example | 15 | VIII | IX | X |
|---|---|---|---|---|
| dimethylpolysiloxane/ polyethylene oxide/ polypropylene oxide copolymer with a cloud point of 42° Celsius | — | 0.50 g | — | — |
| dimethylpolysiloxane/ polyethylene oxide/ polypropylene oxide copolymer with a cloud point of 80° Celsius | — | — | 0.50 g | — |
| ethanol | 41.00 g | 40.00 g | 40.00 g | |
| chitosan | 1.00 g | 1.00 g | 1.00 g | 1.00 g |
| pyrrolidone carboxylic acid | 0.85 g | 0.85 g | 0.85 g | 0.85 g |
| water | 56.65 g | 57.65 g | 56.65 g | 98.15 g |
|  | 100.00 g | 100.00 g | 100.00 g | 100.00 g |
| maximum combing force-wet-(mN) | 212 | 250 | 313 | 272 |
| maximum combing force-dry-(mN) | 863 | 1850 | 910 | 1509 |

Tables 4, 5 and 6 clearly show that the strands of hair treated with the composition according to the invention according to Examples 12, 13, 14 and 15 have a distinctly improved wet and dry combability (reduced maximum combing force).

Example D

Waving Stability

For the purpose of determining waving stability, a strand of hair consisting of 100 hairs was first coiled onto a spiral curler with a diameter of 5 mm and then treated with one of the compositions according to Examples 15, VIII, IX and X of the compositions indicated in Table 6. The strands of hair were then dried, the curlers removed and the length of the hair strands was measured (linear distance between opposite ends).

The strand of hair was then suspended for 22 hours in a closet at 65% relative humidity at 20° Celsius. The length of the hair strand was then measured again.

The waving effect was calculated from the obtained values by means of the following equation:

$$\text{waving stability } \% = \frac{L_0 - L}{L_0 - L_1} \times 100,$$

where
$L_o$=initial length of hair strand
$L$=length of hair strand after treatment
$L_1$=length of hair strand in coiled state.

The results of this comparison text are compiled in the following Table 7.

TABLE 7

| Example | 15 | VIII | IX | X |
|---|---|---|---|---|
| waving stability % | 77.8 | 76.3 | 71.6 | 61.5 |

The tests for waving stability show that the compositions according to the invention not only have measurably improved wet and dry combability, but also have better fixing characteristics than the compositions of the prior art.

We claim:

1. Hair fixing composition in the form of an aqueous solution, foam or gel and containing from 0.1 to 5 percent by weight of a film-forming natural polymer consisting of chitosan; from 5 to 60 percent by weight of at least one water-soluble, halogen-free organic solvent selected from the group consisting of $C_1$- to $C_4$-alcohols, $C_1$- to $C_4$-glycols, esters of polyethylene glycol and $C_2$- to $C_{20}$-carboxylic acids, liquid polyethylene glycols, alkyl ethers of polyethylene glycol and $C_1$- to $C_4$-alcohols and ketones of $C_1$- to $C_5$-alcohols; from 30 to 95 percent by weight of water and 0.05 to 2 percent by weight of at least one compound, wherein said at least one compound is water insoluble at room temperature, but soluble in the composition, and is selected from the group consisting of $C_8$- to $C_{20}$-alkanediols, $C_8$- to $C_{20}$-alkanetriols, monoglycerides of $C_{12}$- to $C_{20}$ fatty acids, monodiglycerides of $C_{12}$- to $C_{20}$-fatty acids, $C_{12}$- to $C_{20}$-fatty alcohols ethoxylated with from 2 to 3 moles of ethylene oxide, polysiloxane/polyether copolymers having a cloud point at a temperature of less than 20° C., polyoxyethylene/polyoxypropylene block polymers and polyoxyethylene/polyoxybutylene block polymers; and wherein said at least one organic solvent and said at least one compound are present in a weight ratio of from 1000:1 to 2.5:1.

2. Hair fixing composition as defined in claim 1, further comprising from 0.01 to 2 percent by weight of a direct dye for simultaneously dyeing hair, and wherein said direct dye is absorbed directly on the hair to dye the hair.

3. Hair fixing composition as defined in claim 2, wherein said direct dye is selected from the group consisting of aromatic nitro dyes, azo dyes anthraquinone dyes and triphenylmethane dyes.

4. Hair fixing composition as defined in claim 1, further comprising from 2 to 10 percent by weight of a propellant selected from the group consisting of n-butane, i-butane, propane, difluorochloromethane, trichloromonofluoromethane, tetrafluorodichloroethane, dimethyl ether, $N_2$, $N_2O$, $CO_2$ and mixtures thereof.

5. Hair fixing composition as defined in claim 1, containing from 0.1 to 0.5% by weight of said at least one compound, water insoluble at room temperature, but soluble in the composition, and said at least one compound consists of at least one of said $C_{12}$- to $C_{20}$-fatty alcohols ethoxylated with from 2 to 3 moles of said ethylene oxide.

6. Hair fixing composition as defined in claim 1, wherein said at least one compound, water insoluble at room temperature, but soluble in the composition, is selected from the group consisting of oleyl alcohol ethoxylated with from 2 to 3 moles of said ethylene oxide, lauryl alcohol ethoxylated with from 2 to 3 moles of said ethylene oxide and cetyl alcohol ethoxylated with 2 moles of said ethylene oxide and said polysiloxane/polyether copolymers having a cloud point at a temperature of less than 20° C.

7. Hair fixing composition as defined in claim 1, wherein said at least one water-soluble, halogen-free organic solvent is selected from the group consisting of ethanol and isopropanol.

* * * * *